US008828068B2

(12) United States Patent
Arcot-Krishnamurthy et al.

(10) Patent No.: US 8,828,068 B2
(45) Date of Patent: Sep. 9, 2014

(54) SYSTEMS AND METHODS FOR LOCAL VASOACTIVE RESPONSE USING TEMPERATURE MODULATION

(75) Inventors: Shantha Arcot-Krishnamurthy, Roseville, MN (US); Allan C. Shuros, St. Paul, MN (US); Jihong Qu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2009 days.

(21) Appl. No.: 11/779,162

(22) Filed: Jul. 17, 2007

(65) Prior Publication Data

US 2009/0024194 A1    Jan. 22, 2009

(51) Int. Cl.
*A61F 7/12* (2006.01)
*A61F 7/00* (2006.01)

(52) U.S. Cl.
CPC ........... *A61F 7/12* (2013.01); *A61F 2007/0075* (2013.01); *A61F 7/123* (2013.01); *A61F 2007/126* (2013.01); *A61F 2007/0071* (2013.01); *A61F 2007/0056* (2013.01)
USPC ............................................. 607/113; 607/96

(58) Field of Classification Search
USPC .................. 607/96, 98–106, 113; 606/27–31
See application file for complete search history.

(56) References Cited

U.S. PATENT DOCUMENTS

| | | | |
|---|---|---|---|
| 3,399,536 A | 9/1968 | Walz | |
| 5,417,689 A | 5/1995 | Fine | |
| 5,496,311 A * | 3/1996 | Abele et al. | ............. 606/28 |
| 5,540,679 A * | 7/1996 | Fram et al. | ............. 606/27 |
| 5,617,868 A | 4/1997 | Harada et al. | |
| 6,277,082 B1 | 8/2001 | Gambale | |
| 6,514,245 B1 | 2/2003 | Williams et al. | |
| 6,522,926 B1 | 2/2003 | Kieval et al. | |
| 6,685,731 B2 | 2/2004 | Kushnir et al. | |
| 6,755,026 B2 | 6/2004 | Wallach | |
| 6,811,551 B2 | 11/2004 | Dae et al. | |
| 6,850,801 B2 | 2/2005 | Kieval et al. | |

(Continued)

FOREIGN PATENT DOCUMENTS

| | | |
|---|---|---|
| WO | WO-2004/064622 A2 | 8/2004 |
| WO | WO-2005084389 | 9/2005 |
| WO | WO-2006/065610 A2 | 6/2006 |
| WO | WO-2007/048068 A2 | 4/2007 |

OTHER PUBLICATIONS

Mustafa, S., et al., "Cooling-induced carotid artery dilatation: an experimental study in isolated vessels", *Stroke*, 33(1), (2002), 256-60.

(Continued)

*Primary Examiner* — Ahmed Farah
(74) *Attorney, Agent, or Firm* — Schwegman Lundberg & Woessner, P.A.

(57) ABSTRACT

Disclosed herein, among other things, is a device for providing a localized vasomodulation of a vessel. According to an embodiment, the device includes a thermal element configured to conduct thermal energy between the thermal element and a desired region of the vessel wall to elicit the localized vasomodulation of the vessel at the desired region. The device also includes a controller operationally connected to the thermal element. The controller is adapted to control the conduction of thermal energy between the thermal element and the desired region of the vessel wall to control the localized vasomodulation of the vessel at the desired region. In various embodiments, a sensor connected to the device provides feedback to the controller.

23 Claims, 5 Drawing Sheets

(56) References Cited

U.S. PATENT DOCUMENTS

| | | | |
|---|---|---|---|
| 6,985,774 B2 | 1/2006 | Kieval et al. | |
| 7,122,047 B2 | 10/2006 | Grahn | |
| 7,842,076 B2 * | 11/2010 | Zikorus et al. | 607/96 |
| 2002/0045924 A1 * | 4/2002 | Fox | 607/96 |
| 2002/0077665 A1 * | 6/2002 | Kordis et al. | 607/1 |
| 2005/0070962 A1 | 3/2005 | Echt et al. | |
| 2005/0149130 A1 * | 7/2005 | Libbus | 607/9 |
| 2005/0240249 A1 * | 10/2005 | Tu et al. | 607/96 |
| 2005/0251212 A1 | 11/2005 | Kieval et al. | |
| 2007/0135875 A1 | 6/2007 | Demarais et al. | |
| 2008/0132972 A1 * | 6/2008 | Shuros et al. | 607/60 |

OTHER PUBLICATIONS

Shuros, Allan C., et al., "Method and Device for Cardiac Vasoactive Therapy", U.S. Appl. No. 11/566,896, filed Dec. 5, 2006, 29 pgs.

"Japanese Application Serial No. 2010-514756, Office Action mailed Apr. 2, 2012", With English Translation, 4 pgs.

"Japanese Application Serial No. 2010-514756, Office Action mailed Sep. 30, 2011", (w/ English Translation), 6 pgs.

"Japanese Application Serial No. 2010-514756, Response filed Dec. 28, 2011 to Office Action mailed Sep. 30, 2011", (w/ English Translation of Amended Claims), 7 pgs.

"International Application Serial No. PCT/US2008/007299, International Search Report mailed Oct. 21, 2008", 4 pgs.

"International Application Serial No. PCT/US2008/007299, Written Opinion mailed Oct. 21, 2008", 6 pgs.

"Radiant Medical Home Page", [online]. [archived Dec. 11, 2004]. Retrieved from the Internet: <URL: http://web.archive.org/web/20041211223605/http://www.radiantmedical.com/>, 1 pg.

"European Application Serial No. 08768355.3, Examination Notification Art. 94(3) mailed Jun. 21, 2013", 3 pgs.

"European Application Serial No. 08768355.3, Response filed Nov. 4, 2013 to Examination Notification Art. 94(3) mailed Jun. 21, 2013", 9 pgs.

* cited by examiner

SYSTEMS AND METHODS FOR LOCAL VASOACTIVE RESPONSE USING TEMPERATURE MODULATION

TECHNICAL FIELD

This disclosure relates generally to implantable medical devices, and more particularly to systems and methods for temperature modulation for vasoactive response.

BACKGROUND

Coronary artery disease (CAD) occurs when the coronary arteries that supply blood to the myocardium become hardened and narrowed due to the buildup of atherosclerotic plaque. An atherosclerotic plaque is the site of an inflammatory reaction within the wall of an artery and is made up of a core containing lipid and inflammatory cells surrounded by a connective tissue capsule. A myocardial infarction (MI), or heart attack, occurs when atherosclerotic plaque within a coronary artery ruptures and leads to the clotting of blood (thrombosis) within the artery by exposing the highly thrombogenic lipid core of the plaque to the blood. The complete or nearly complete obstruction to coronary blood flow can damage a substantial area of heart tissue and cause sudden death, usually due to an abnormal heart rhythm that prevents effective pumping.

It is generally accepted that physical activity and fitness improve health and reduce mortality. Studies have indicated that aerobic training improves cardiac autonomic regulation, reduces heart rate and is associated with increased cardiac vagal outflow. Physical conditioning can be considered to be a repetitive, high-level exercise that occurs intermittently over time.

Improved systems and methods for controlling blood flow are needed.

SUMMARY

Disclosed herein, among other things, is a device for locally modulating temperature for a vasoactive response. For example, in certain situations it is desirable to increase blood flow in coronary vessels. One example includes patients with coronary artery disease (CAD). Further, in other situations it is desirable to decrease blood flow in a coronary vessel. One example includes conditioning therapy. Temporary constriction can function as a physical conditioning therapy to intermittently stress the heart to improve the overall health of the organ. Physical conditioning therapy can be applied as therapy for heart failure. Examples of other physical conditioning therapies include therapies for patients who are unable to exercise. For example, a morbidly obese patient may be unable to exercise, but may still benefit from the physical conditioning therapy. Furthermore, patients with injuries such as joint injuries that prevent them from performing their normal physical activities may benefit from the physical conditioning therapy. According to an embodiment, the device includes a thermal element configured to conduct thermal energy between the thermal element and a desired region of the vessel wall to elicit the localized vasomodulation of the vessel at the desired region. The device also includes a controller operationally connected to the thermal element. The controller is adapted to control the conduction of thermal energy between the thermal element and the desired region of the vessel wall to control the localized vasomodulation of the vessel at the desired region.

Disclosed herein, among other things, is a method for modulating temperature for a vasoactive response. According to an embodiment, a thermal element is placed in thermal contact with a vessel wall. The vessel is selectively cooled with the thermal element to constrict the vessel proximate to where the thermal element is in thermal contact with the vessel, in various embodiments. The vessel is selectively warmed with the thermal element to dilate the vessel proximate to where the thermal element is in thermal contact with the vessel, in various embodiments.

Disclosed herein, among other things, is a method for controlling blood flow. According to an embodiment, a thermal element is placed in thermal contact with a vessel wall. A thermal effect is selectively produced on the vessel wall proximate to where the thermal element is in contact with the vessel, to constrict or dilate the vessel to control blood flow.

Disclosed herein, among other things, is a method for controlling blood flow in a closed-loop system. According to an embodiment, at least one parameter indicative of blood flow is sensed. Some embodiments automatically cool the vessel using a thermal element at the distal end of an implantable lead using the at least one parameter to decrease flow, and some embodiments automatically warm the vessel using a thermal element at the distal end of an implantable lead using the at least one parameter to increase flow.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1:
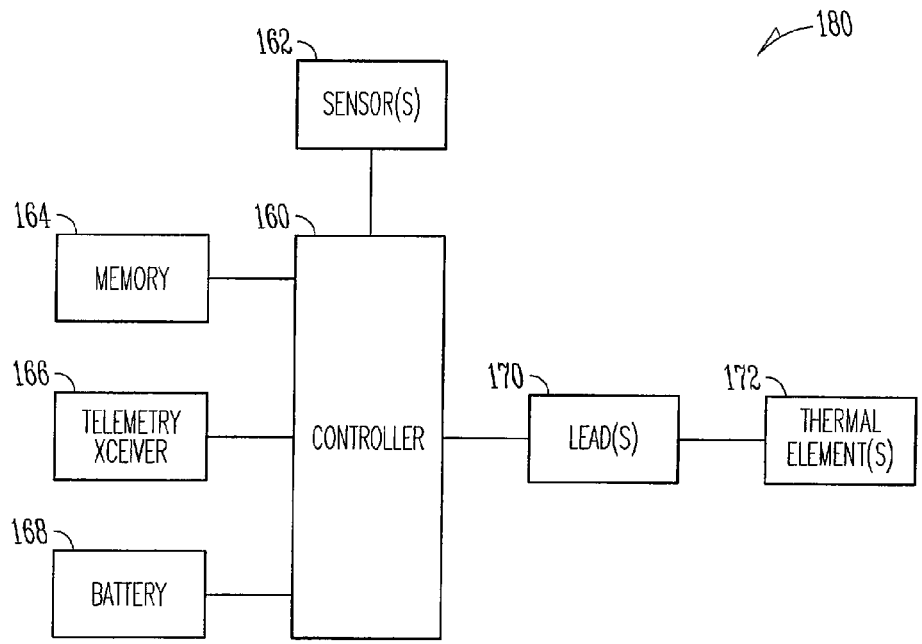
FIG. 1 illustrates an embodiment of a device for providing a localized vasomodulation of a vessel.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter generally relates to modulating temperature to cause a desired vasoactive response that changes the cross-sectional area of a vessel and thereby changes the ability of the vessel to permit blood flow. Vasoactive response may also be referred to as vasomodulation therapy. A vasodilation response increases the vessel size and corresponding fluid flow through the vessel. Local tissue temperature is increased using a lead or catheter system to stimulate the vasodilation response. The vessel dilates to bring the local temperature back to normal (or maintain homeostasis). The temperature increase mimics an increase in local metabolic demand, causing dilation. The dilation can be triggered intermittently or as pre- or post-conditioning during episodes of natural ischemia. An embodiment uses an ischemia detection/prediction system to sense ischemic episodes and trigger therapy based on the detection. The device can apply therapy to vasodilate coronary arteries to prevent myocardial infarction.

A vasoconstriction response decreases the vessel size and corresponding fluid flow through the vessel. Local tissue temperature is decreased using a lead or catheter system to stimulate the vasoconstriction response. This stimulated vasoconstriction produces intermittent stress in the form of ischemia, which can be therapeutic similar to exercise and may lead to angiogenesis and vessel collateralization. Cooling can also reduce metabolic demand, such as post-myocardial infarction, during tachycardia, or gene or cell therapy delivery. Vasoconstriction and vasodilation therapies may be independent or combined into one device system with closed-loop feedback and therapy mechanisms. Stimulation for intermittent vasoactive response can be combined with other therapies, including traditional pacing therapy, to alter regional stress.

A system embodiment includes a device, such as a pulse generator with a lead or catheter having one or more thermal elements adapted to modulate temperature. Some system embodiments include a lead with one or more poles coated with materials of higher resistance. The poles have a heating element that heats up when electrical impulse is delivered. An electrical impulse can be modified to be larger in amplitude or duration to increase heating. Some system embodiments have a cooling effect. Cooling can be accomplished using a refrigeration system, such as a compressor within the device and circulating coolant through a lead or catheter for thermal transfer to tissue in thermal contact with the thermal element. An embodiment of the refrigeration system includes a Freon-based compressor. Heating and cooling can also be accomplished using a Peltier module, as discussed below with respect to FIG. 3. Temperature sensors can be used to monitor temperature to be within a threshold range.

FIG. 1 illustrates an embodiment of a device 180 for providing a localized vasomodulation of a vessel. According to an embodiment, the device includes a thermal element 172 configured to conduct thermal energy between the thermal element and a desired region of the vessel wall to elicit the localized vasomodulation of the vessel at the desired region. The device also includes a controller 160 operationally connected to the thermal element. The controller is adapted to control the conduction of thermal energy between the thermal element and the desired region of the vessel wall to control the localized vasomodulation of the vessel at the desired region. In various embodiments, one or more sensors 162 connected to the device provide feedback to the controller.

According to an embodiment, the thermal element is adapted to conduct thermal energy to vasomodulate a length of the vessel less than 2 centimeters without substantially modulating portions of the vessel downstream or upstream from the desired region. The thermal element is adapted to conduct thermal energy to vasomodulate microvessels of the targeted organ without substantially modulating portions of the vessel downstream or upstream from the desired region, in an embodiment. The controller can be adapted to control a length of time during which thermal energy is conducted between the thermal element and the desired region of the vessel wall. The controller can be adapted to control a temperature of the thermal element. Some embodiments include a temperature sensor adapted to provide feedback to the controller. In various embodiments, the thermal element (such as a resistive element or a Peltier module, for example) is configured to conduct thermal energy from the thermal element to the desired region of the vessel wall to elicit a localized vasodilation of the vessel at the desired region of the vessel wall. The thermal element (such as circulated coolant from a refrigeration system, or a Peltier module, for example) is configured to conduct thermal energy from the desired region of the vessel wall to the thermal element to elicit a localized vasoconstriction of the vessel at the desired region of the vessel wall.

According to an embodiment, the device includes a memory 164 and a therapy schedule stored in the memory. The controller can be adapted to control the conduction of thermal energy according to the therapy schedule. The device can further include an activity sensory, and the controller can be adapted to control the conduction of thermal energy using the activity sensor. Some embodiments include an ischemia detector, and the controller can be adapted to control the conduction of thermal energy using the ischemia detector. The device can further include a temperature sensor, and controller can be adapted to control the conduction of thermal energy using feedback from the temperature sensor.

According to an embodiment, the device 180 includes lead 170 to connect the thermal element 172 to the controller. However, leadless and/or wireless devices can be used without departing from the scope of this disclosure. The thermal element 172 is in thermal contact with a vessel and adapted to heat or cool the vessel to dilate or constrict the vessel proximate to where the thermal element thermally contacts the vessel. The controller 160 can be adapted to control the amount and duration of heating or cooling. In various embodiments, the thermal element 172 includes a resistor for heating, a Peltier module (such as shown in FIG. 3) for heating and cooling, and/or a circulated coolant from a refrigeration system for cooling.

A battery 168 supplies power to the circuitry. The controller 160 controls the overall operation of the device in accordance with programmed instructions and/or circuit configurations. The controller 160 can be implemented as a microprocessor-based controller and include a microprocessor and memory 164 for data and program storage, implemented with dedicated hardware components such as application-specific integrated circuits (ASICs, e.g., finite state machines), or implemented as a combination thereof. The controller 160 also includes timing circuitry such as external clocks for implementing timers used to measure lapsed intervals and schedule events. As the term is used herein, the programming of the controller refers to either code executed by a microprocessor or to specific configurations of hardware components for performing particular functions. In one embodiment, interfaced to the controller are sensing circuitry and pulse generation circuitry by which the controller interprets sensing signals and controls the delivery of stimulation pulses. The pulse generation circuitry can also include a shocking pulse generator for delivering a defibrillation/cardioversion shock via a shock electrode upon detection of a tachyarrhythmia. A telemetry transceiver 166 is interfaced to the controller which enables the controller to communicate with an external programmer and/or a remote monitoring unit. Also interfaced to the controller are one or more sensors 162 for sensing physiological variables that can be used to control pacing or vasoactive temperature stimulation such as activity level (e.g., an accelerometer), temperature, heart rate, minute ventilation, thoracic impedance indicating cardiac blood flow and/or timing of cardiac cycles, cardiac output, blood pressure, blood oxygen, blood pH, blood enzymes (e.g. CK-MB, troponin, etc) and myocardial contractility (e.g., as indicated by the maximum dP/dt measured by an arterial pressure sensor). When vasomodulation therapy includes a cerebral target, a stroke sensor can be used to sense pressure or enzyme levels. When vasomodulation therapy includes a renal target, sensors such as pressure, local flow measurement, ion concentration and osmolality can be used.

Figure 2:
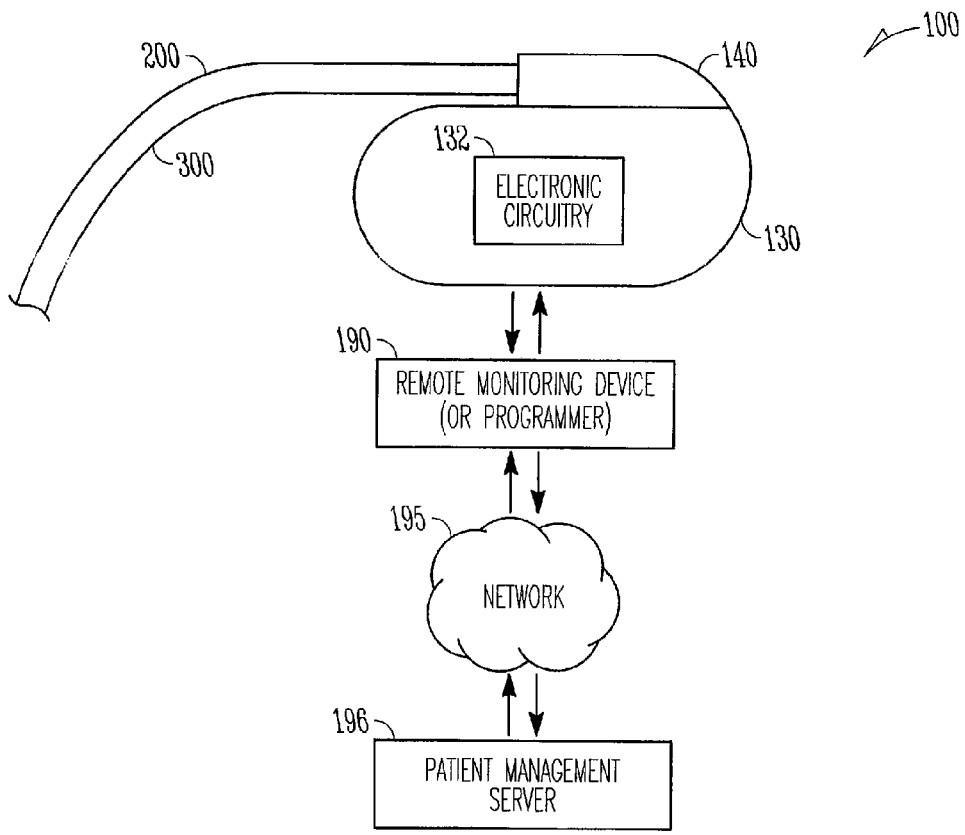
FIG. 2 illustrates an embodiment of a system for modulating temperature for a vasoactive response including a medical device.

FIG. 2 illustrates an embodiment of a system for modulating temperature for a vasoactive response including a medical device. A device 100, which is shown as an implantable device but can include external devices in varying embodiments, includes a hermetically sealed housing 130 that is placed subcutaneously or submuscularly in a patient's chest. The housing 130 can be formed from a conductive metal, such as titanium, and can serve as an electrode for delivering electrical stimulation or sensing in a unipolar configuration. A header 140, which can be formed of an insulating material, is mounted on the housing 130 for receiving leads 200 and 300 which can be then electrically connected to temperature control circuitry, pulse generation circuitry and/or sensing circuitry. Contained within the housing 130 is the electronic circuitry 132 for providing the functionality to the device as described herein which can include a power supply, sensing circuitry, temperature control circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device, defined as a device at a location remote from the patient, also communicates via telemetry with the device 100 and can be further interfaced to a network 195 (e.g., an internet connection) for communicating with a patient management server 196 that allows clinical personnel at remote locations to receive data from the remote monitoring device as well as issue commands. The controller can be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
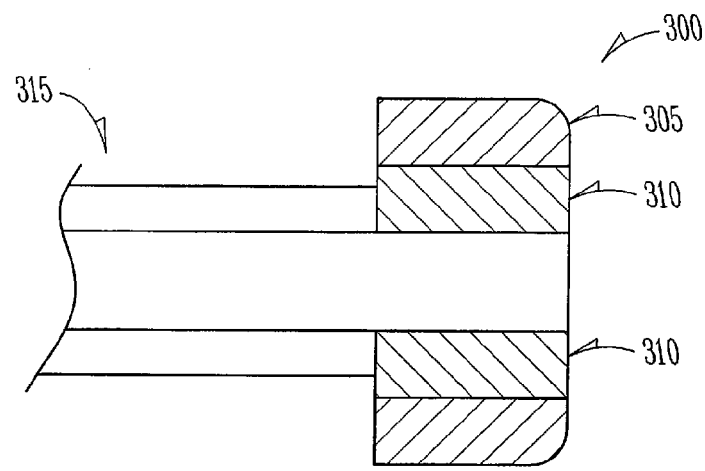
FIG. 3 illustrates an embodiment of a thermal element for modulating temperature for a vasoactive response.

FIG. 3 illustrates an embodiment of a thermal element for modulating temperature for a vasoactive response. The depicted thermal element is a Peltier module 300, which in an embodiment includes the tip of an electrode connected to a lead 315. The module 300 includes a tissue contacting side 305 and a blood contacting side 310. In various embodiments, the tissue contacting side 305 cools the tissue in the vicinity of the element. The blood contacting side 310, or heat sink, can be used to dissipate heat through the blood stream, in various embodiments. A Peltier module or thermoelectric device creates a temperature gradient from an electrical voltage. This occurs when a current is passed through two dissimilar materials (metals or semiconductors, for example) that are connected to each other at two junctions (Peltier junctions). The current drives a transfer of heat from one junction to the other, so one junction cools off while the other heats up. An embodiment of a Peltier module includes semiconductors mounted successively, forming p-n and n-p junctions. Each junction has a thermal contact with radiators. When switching on the current of a definite polarity, a temperature difference forms between the radiators, one warms up and the other works as a refrigerator. Switching polarity will have the opposite effect, so one element can be used for both heating and cooling (both vasodilation and vasoconstriction). As mentioned, other types of thermal elements, such as resistors and circulated coolant, can be used without departing from the scope of the disclosure. When using a resistance-type heating element, electrical stimulation parameters (such as amplitude, pulse duration, duty cycle, number of pulses and polarity) can be modulated to illicit a temperature change. An epicardial lead or patch can be used for increased contact area. The thermal element can be adapted to be positioned to heat or cool a local region of a vessel wall to provide a local vasoactive response. In an embodiment targeting an artery, a section of less than 5 centimeters is heated or cooled to provide a vasoactive response along that length. In another embodiment targeting an artery, a section of less than 2 centimeters is heated or cooled to provide a vasoactive response along that length. Microvessels may be modulated (dilated or constricted) in an embodiment. An example includes a stimulating electrode (or other thermal element) positioned on/in the myocardium, targeting arterioles and/or capillaries.

Figure 4:
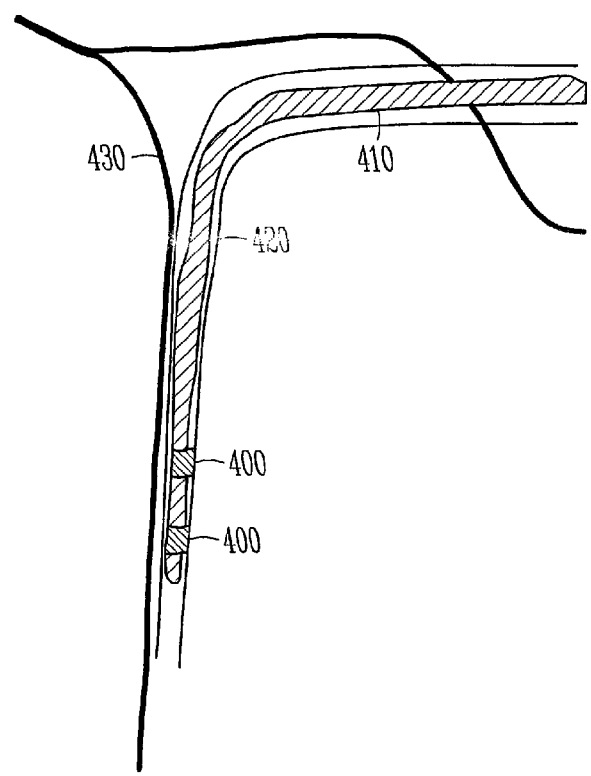
FIG. 4 illustrates embodiments of vasoactive thermal elements.

A thermal element can be positioned directly on a blood vessel and connected to the device, which stimulates periodically or intermittently for a vasoactive response. Alternatively, the lead can be placed as in FIG. 4, which shows embodiments of vasoactive thermal elements 400 incorporated into a lead 410 that is inserted into the coronary sinus or a cardiac vein 420 so as to be in proximity to a branch of a coronary artery 430, such as the proximal left circumflex coronary artery. The lead 410 can incorporate mechanical means to facilitate positioning the stimulation electrodes within a vein adjacent the coronary artery to be stimulated. Applications for this thermal therapy are not limited to a particular vessel, but can be widely applied to areas in the atria, ventricular areas including infarct, border zone, and healthy tissue, cardiac blood vessel, and larger blood vessels such as the aorta, renal arteries (to affect filtration rates and ion concentrations), and cerebral arteries (to address feinting or stroke).

Figure 5A:
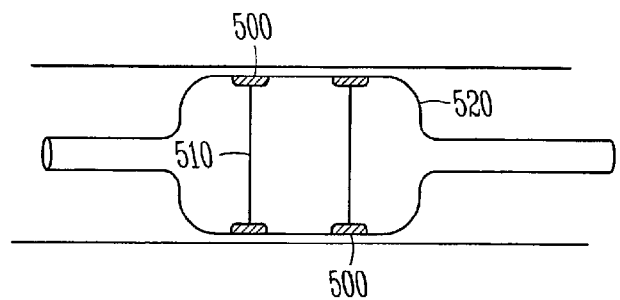
FIGS. 5A and 5B illustrate some vasoactive lead embodiments.
Figure 5B:
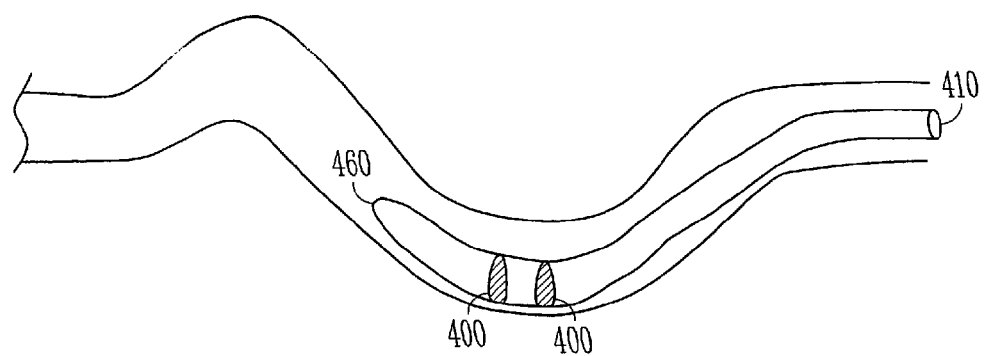

FIG. 5A shows one embodiment in which the lead incorporates a stent 520 with thermal elements 500 on struts 510 that expand against vein wall and thus press the electrodes against the adjacent artery wall. FIG. 5B shows an embodiment in which the lead 410 has a steerable tip 460 that can be maneuvered in such a way as to press the thermal elements 400 against the adjacent artery wall. A stimulation lead can be placed in the right ventricle to target the right coronary artery. A stimulation lead can be placed in the myocardium in a region determined to have microvascular dysfunction. Some patients with anginal symptoms may not have occlusive lesions in their major arteries. However, the problem arises in these patients in their microvascular circulation. The vasomodulation therapy may be applied to these patients by targeting their myocardial capillary bed. After implantation and appropriate placement of the vasoactive stimulation thermal elements, the device can then be programmed with appropriate stimulation parameters to deliver vasoconstriction and/or vasodilation stimulation.

A number of methods can be used with the described system to provide therapy. An example is intermittent on/off therapy, where periods of vasoconstriction/dilation are applied for intermittent stress (therapeutic, or pre- or post-conditioning for myocardial infarction (MI) or angina), such as for five minutes per day on a pre-programmed schedule. Another example is triggered vasodilation for exercise. In this example, a sensor, such as an accelerometer, is used to detect activity or exercise and turns on therapy to dilate coronary arteries. A further example is triggered vasodilation for MI, in which ischemic events are detected for targeted vasodilation. Another example is triggered local metabolic demand reduction, in which local cooling is used to reduce demand following MI, tachy episodes, atrial fibrillation and gene or cell delivery.

Figure 6:
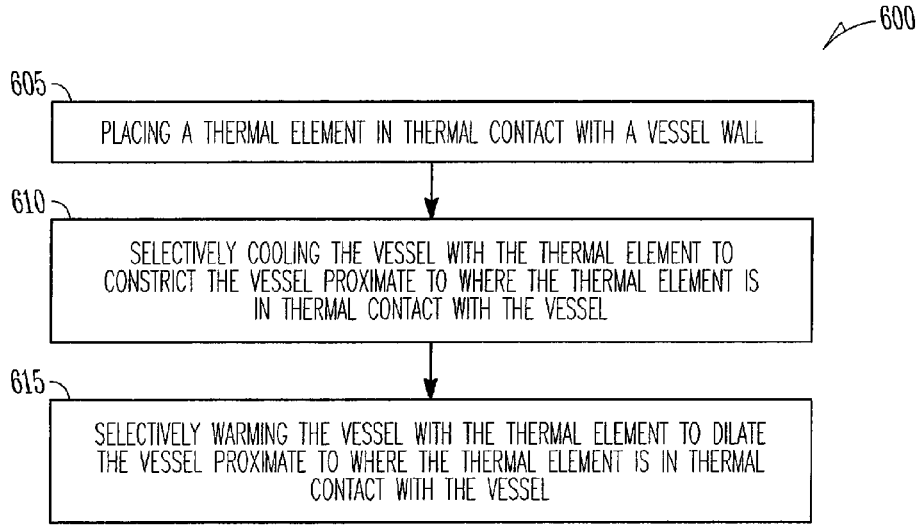
FIG. 6 illustrates an embodiment of a method for modulating temperature for a vasoactive response.

FIG. 6 illustrates an embodiment of a method 600 for modulating temperature for a vasoactive response. According to an embodiment, a thermal element is placed in thermal contact with a vessel wall, at 605. At 610, the vessel is selectively cooled with the thermal element to constrict the vessel proximate to where the thermal element is in thermal contact with the vessel, in various embodiments. At 615, the vessel is selectively warmed with the thermal element to dilate the vessel proximate to where the thermal element is in thermal contact with the vessel, in various embodiments.

According to an embodiment, the thermal element is placed in physical contact with the vessel wall. The thermal element is placed in a location operationally adjacent to the vessel wall, such as in a vein adjacent a targeted artery wall, in various embodiments. In various embodiments, additional therapies are provided in conjunction with selectively warming or cooling the vessel, such as pacing therapy, non-excitatory pacing therapy, and/or drug delivery therapy. Some embodiments sense a parameter, such as temperature of the vessel, and adjust the cooling or warming based on the sensed parameter, in a closed-loop system. In one embodiment, selectively cooling or warming the vessel includes intermittently cooling or warming the vessel.

Figure 7:
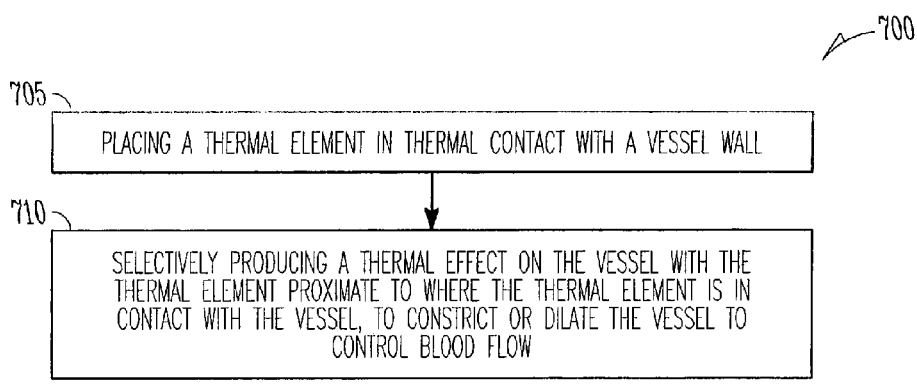
FIG. 7 illustrates an embodiment of a method for controlling blood flow.

FIG. 7 illustrates an embodiment of a method 700 for controlling blood flow. According to an embodiment, a thermal element is placed in thermal contact with a vessel wall, at 705. At 710, a thermal effect is selectively produced on the vessel with the thermal element proximate to where the thermal element is in contact with the vessel, to constrict or dilate the vessel to control blood flow. A parameter indicative of blood flow can sensed and used to control the thermal effect. An embodiment includes selectively cooling the vessel with the thermal element to constrict the vessel proximate to where the thermal element is in contact with the vessel, in one embodiment. The vessel can be selectively warmed with the thermal element to dilate the vessel proximate to where the thermal element is in contact with the vessel. In various embodiments, the targeted vessel includes a cardiac artery. One of skill in the art will appreciate that other vascular targets are possible without departing from the scope of this disclosure.

Figure 8:
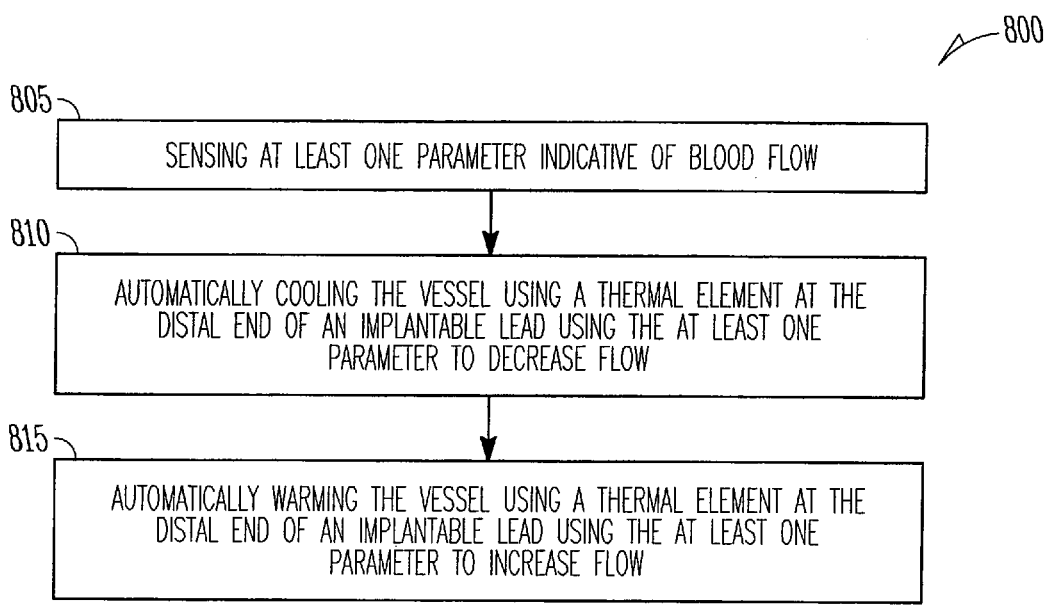
FIG. 8 illustrates an embodiment of a method for controlling blood flow in a closed-loop system.

FIG. 8 illustrates an embodiment of a method 800 for controlling blood flow in a closed-loop system. According to an embodiment, at least one parameter indicative of blood flow is sensed, at 805. At 810, the vessel is automatically cooled using a thermal element at the distal end of an implantable lead using the at least one parameter to decrease flow, in various embodiments. At 815, the vessel is automatically warmed using a thermal element at the distal end of an implantable lead using the at least one parameter to increase flow, according to various embodiments. In one embodiment, automatically cooling the vessel includes producing intermittent stress in the form of ischemia by inducing vasoconstriction. In an embodiment, automatically warming the vessel includes inducing vasodilation as pre- or post-conditioning during episodes of ischemia.

Vasomodulation therapy is beneficial in a number of circumstances. For patients with angina or coronary heart disease (CHD), vasomodulation will elevate symptoms, elicit angiogenesis, and reduce vessel stiffening. For patients post-MI and heart failure (HF) patients, intermittent vasomodulation can prevent progression of these diseases. In addition, for patients with reduced exercise capacity, myocardial perfusion can be increased using vasomodulation therapy. Vasomodulation therapy is further useful to decrease adverse side effects of drug therapy. Also, vasomodulation using the described system provides direct device control of coronary flow and local metabolic demand.

Although specific embodiments have been illustrated and described herein, it will be appreciated by those of ordinary skill in the art that any arrangement which is calculated to achieve the same purpose may be substituted for the specific embodiment shown. It is to be understood that the above description is intended to be illustrative, and not restrictive. The scope of the present subject matter should be determined with reference to the appended claims, along with the full scope of equivalents to which such claims are entitled.

We claim:

1. A device for providing a localized vasomodulation of a vessel having a vessel wall, the device comprising:
   a thermal element configured to conduct thermal energy between the thermal element and a desired region of the vessel wall to elicit the localized vasomodulation of the vessel at the desired region;
   a controller operationally connected to the thermal element, the controller adapted to control the conduction of thermal energy between the thermal element and the desired region of the vessel wall to control the localized vasomodulation of the vessel at the desired region;
   a memory; and
   a therapy schedule stored in the memory,
   wherein the controller is adapted to control the conduction of thermal energy according to the therapy schedule.

2. The device of claim 1, wherein the thermal element is adapted to conduct thermal energy to vasomodulate a length of the vessel less than 2 centimeters without modulating portions of the vessel downstream from the desired region.

3. The device of claim 1, wherein the thermal element is adapted to conduct thermal energy to vasomodulate microvessels of a targeted organ without modulating portions of the vessel upstream from the desired region.

4. The device of claim 1. wherein the controller is adapted to control a length of time during which thermal energy is conducted between the thermal element and the desired region of the vessel wall.

5. The device of claim 1, wherein the thermal element is configured to conduct thermal energy from the thermal element to the desired region of the vessel wall to elicit a localized vasodilation of the vessel at the desired region of the vessel wall.

6. The device of claim 5, wherein the thermal element includes a resistive element.

7. The device of claim 5,wherein the thermal element includes a Peltier module.

8. The device of claim 1, wherein the thermal element is configured to conduct thermal energy from the desired region of the vessel wall to the thermal element to elicit a localized vasoconstriction of the vessel at the desired region of the vessel wall.

9. The device of claim 8, wherein the thermal element includes circulated coolant.

10. The device of claim 1, further comprising:
an activity sensory, wherein the controller is adapted to control the conduction of thermal energy using the activity sensor.

11. The device of claim 1, further comprising:
an ischemia detector, wherein the controller is adapted to control the conduction of thermal energy using the ischemia detector.

12. The device of claim 1, further comprising:
a temperature sensor, wherein the controller is adapted to control the conduction of thermal energy using feedback from the temperature sensor.

13. The device of claim 1, further comprising a sensor configured to sense a parameter indicative of blood flow.

14. The device of claim 13, wherein the controller is adapted to control the conduction of thermal energy using feedback from the sensor.

15. The device of claim 14, wherein the controller is adapted to control the conduction of thermal energy to cool the vessel to decrease blood flow.

16. The device of claim 14, wherein the controller is adapted to control the conduction of thermal energy to warm the vessel to increase blood flow.

17. The device of claim 1, wherein the controller is adapted to control the conduction of thermal energy to intermittently cool the vessel, thereby intermittently inducing vasoconstriction to produce intermittent stress in the form of ischemia.

18. The device of claim 1, wherein the controller is adapted to control the conduction of thermal energy to warm the vessel to induce vasodilation as pre-conditioning during episodes of ischemia.

19. The device of claim 1, wherein the controller is adapted to control the conduction of thermal energy to warm the vessel to induce vasodilation as post-conditioning following episodes of ischemia.

20. A device for providing a localized vasomodulation of a vessel having a vessel wall, the device comprising:
a thermal element configured to conduct thermal energy between the thermal element and a desired region of the vessel wall to elicit the localized vasomodulation of the vessel at the desired region;
a controller operationally connected to the thermal element, the controller adapted to control the conduction of thermal energy between the thermal element and the desired region of the vessel wall to control the localized vasomodulation of the vessel at the desired region; and
a sensor configured to sense a parameter indicative of blood flow,
wherein the controller is adapted to control the conduction of thermal energy using feedback from the sensor, and wherein the controller is adapted to control the conduction of thermal energy to cool the vessel to decrease blood flow.

21. A device for providing a localized vasomodulation of a vessel having a vessel wall, the device comprising:
a thermal element configured to conduct thermal energy between the thermal element and a desired region of the vessel wall to elicit the localized vasomodulation of the vessel at the desired region; and
a controller operationally connected to the thermal element, the controller adapted to control the conduction of thermal energy between the thermal element and the desired region of the vessel wall to control the localized vasomodulation of the vessel at the desired region,
wherein the controller is adapted to control the conduction of thermal energy to intermittently cool the vessel, thereby intermittently inducing vasoconstriction to produce intermittent stress in the form of ischemia.

22. A device for providing a localized vasomodulation of a vessel having a vessel wall, the device comprising:
a thermal element configured to conduct thermal energy between the thermal element and a desired region of the vessel wall to elicit the localized vasomodulation of the vessel at the desired region; and
a controller operationally connected to the thermal element, the controller adapted to control the conduction of thermal energy between the thermal element and the desired region of the vessel wall to control the localized vasomodulation of the vessel at the desired region,
wherein the controller is adapted to control the conduction of thermal energy to warm the vessel to induce vasodilation as pre-conditioning during episodes of ischemia.

23. A device for providing a localized vasomodulation of a vessel having a vessel wall, the device comprising:
a thermal element configured to conduct thermal energy between the thermal element and a desired region of the vessel wall to elicit the localized vasomodulation of the vessel at the desired region; and
a controller operationally connected to the thermal element, the controller adapted to control the conduction of thermal energy between the thermal element and the desired region of the vessel wall to control the localized vasomodulation of the vessel at the desired region,
wherein the controller is adapted to control the conduction of thermal energy to warm the vessel to induce vasodilation as post-conditioning following episodes of ischemia.

* * * * *